United States Patent [19]
Maier et al.

[11] Patent Number: 4,474,887
[45] Date of Patent: Oct. 2, 1984

[54] METHOD FOR THE DETERMINATION OF LOW DENSITY LIPOPROTEIN

[75] Inventors: Josef Maier; Manfred Gloger, both of Weilheim; Brigitte Dräger, Tutzing, all of Fed. Rep. of Germany

[73] Assignee: Boehringer Mannheim GmbH, Mannheim, Fed. Rep. of Germany

[21] Appl. No.: 409,277

[22] Filed: Aug. 18, 1982

[30] Foreign Application Priority Data

Aug. 27, 1981 [DE] Fed. Rep. of Germany ....... 3133937

[51] Int. Cl.$^3$ ............................................ G01N 33/92
[52] U.S. Cl. ..................................... 436/71; 210/728; 436/13
[58] Field of Search ................... 436/13, 71; 210/728, 210/732

[56] References Cited

U.S. PATENT DOCUMENTS

| 3,955,925 | 5/1976 | Proksch et al. | 260/112 B X |
| 4,039,285 | 8/1977 | Teipel | 436/71 X |
| 4,190,628 | 2/1980 | Sears | 206/569 X |
| 4,215,993 | 8/1980 | Sanders | 436/71 |
| 4,328,000 | 5/1982 | Horn et al. | 436/86 |

Primary Examiner—Arnold Turk
Attorney, Agent, or Firm—Felfe & Lynch

[57] ABSTRACT

The present invention provides a process for the determination of the $\beta$-lipoprotein fraction (LDL) in body fluids, especially in serum or plasma, wherein the LDL fraction is selectively precipitated from the sample by the addition of a polyvinyl sulphate with monovalent cations and then determined.

The present invention also provides a reagent for the determination of the $\beta$-lipoprotein fraction (LDL) in body fluids, especially in serum or plasma, wherein it contains polyvinyl sulphate.

12 Claims, No Drawings

METHOD FOR THE DETERMINATION OF LOW DENSITY LIPOPROTEIN

This invention relates to a method and a reagent for the determination of the β-lipoprotein fraction (low density lipoprotein (LDL)) in body fluids.

Hypercholesterolaemia and hypertriglyceridaemia favor the genesis of atherosclerosis and of heart infarct. Therefore, the determination of cholesterol and of the triglycerides in serum belong to the tests most frequently carried out in routine clinical-chemical laboratories.

Numerous investigations of fat metabolism have come to the conclusion that the individual coronary risk can be better assessed when there is determined not only the change in the triglyceride and cholesterol level but also the fundamental pathological displacements in the lipoprotein pattern (see Munch. med. Wschr., 121, 1693/1979).

The known plasma lipoproteins contain a varyingly high proportion of proteins, phospholipids, cholesterol and triglycerides. On the basis of their behaviour (differing density) in an analytical centrifuge, they can be divided up into three different classes:

pre-β-lipoprotein=VLDL (very low density lipoprotein)
β-lipoprotein=LDL (low density lipoprotein)
α-lipoprotein=HDL (high density lipoprotein)

Investigation of the function of the lipoproteins showed that the LDL within the lipoproteins represents the atherogenic component, the increase of which in the blood indicates an increased risk of coronary disease. Therefore, an early recognition and combating of this state is of great importance. Thus, there is a need for a practical process for the quantitative determination of the LDL concentration in serum and plasma.

Hitherto, for the determination of the LDL lipoprotein fraction, essentially four methods have been used, all of which, however, suffer from certain disadvantages:

1. Ultracentrifuging

This process is not suitable for a routine laboratory since it requires the use of a special equipment of the apparatus and the carrying out thereof requires an extremely careful working technique and a very high expenditure of time (2×20 hours at 105,000 g). Therefore, this analytical process has hitherto been limited to medical research laboratories.

2. Precipitation reaction

The LDL content can also be determined by fractional precipitation with a polyanion, for example heparin sodium or dextran sulphate and a divalent cation, such as calcium manganese or magnesium cations. The lipoproteins can be precipitated out with an increasing concentration of the polyanion in the following sequence: VLDL, LDL and HDL. However, this process requires two working steps and is thus not practical and cannot be automated: VLDL is separated off in a first precipitation stage and subsequently, by increasing the concentration of the precipitation agent, the LDL lipoprotein fraction is precipitated and determined turbidimetrically (see H. Okabe, Xth Int. Cong. of Clin, Chem., Mexico (1978)).

3. Determination of the LDL concentration via the Friedewald formula

In the case of this process, the triglyceride, cholesterol and HDL-cholesterol contents of the sample are determined and the content of LDL cholesterol calculated therefrom the Friedewald's process (see Clin. Chem., 18, 499/1972). However, this laborious process does not give exact values, especially in the case of sera which have a high content of triglycerides.

4. Qualification after electrophoretic separation and polyanion precipitation This process is, however, time-consuming and requires the use of an electrophoresis apparatus, as well as of a densitometer, for the evaluation (see Lab. Med., 1, 145/1977).

It is an object of the present invention to provide a practical process which is capable of automation, with which LDL can be determined directly in a routine laboratory.

Thus, according to the present invention, there is provided a process for the determination of the β-lipoprotein fraction (LDL) in body fluids, such as serum or plasma, wherein the LDL fraction is selectively precipitated from the sample by the addition of a polyvinyl sulphate with monovalent cations and then determined.

The present invention is based upon the discovery of the surprising fact that LDL can be selectively precipitated and determined practically quantitatively in the presence of VLDL and HDL by the addition of a polyvinyl sulphate with monovalent cations. This is surprising since, according to the previously published investigations, when precipitating LDL, VLDL is always co-precipitated if it has not been previously separated (see M. Burstein, H. R. Scholnick in "Protides of the Biological Fluids", ed. Peeters, pp. 21–28/1972; Arztl. Lab., 23, 101–110/1977).

The precipitation treatment according to the present invention is preferably carried out directly in whole serum which has not been pre-treated. The precipitate is separated off, preferably by centrifuging.

By polyvinyl sulphate within the meaning of the present invention, there is to be understood a polymer derived from polyvinyl alcohol in which the hydroxyl groups have been esterified with sulphuric acid. The molecular size is without noticeable influence on the process so long as the product is still sufficiently water-soluble. However, at least 70% of the vinyl alcohol units should preferably contain a sulphate ester group. The degree of esterification is preferably at least 80% and more preferably at least 90%.

The amount of polyvinyl sulphate necessary in each particular case can easily be determined by simple preliminary experiments, 0.1 to 0.01% by weight of polyvinyl sulphate preferably being used per unit volume of sample solution. The addition of the polyvinyl sulphate in the form of a dilute aqueous solution containing about 1 to 20 g. polyvinyl sulphate (PVS) per liter has proved to be preferable. However, the process of the present invention can also be carried out with the use of concentrated PVS solutions and also by the addition of PVS in solid form if the sample solution can be sufficiently well stirred. However, since, as a rule, the amounts of sample solution used are very small, the addition of PVS in the form of a dilute solution is preferred. Thus, for example, 200 parts by volume of serum can be mixed with 40 parts by volume of a 0.1 to 1% PVS solution. Especially good results have been obtained with a 0.2 to 0.5% aqueous solution which is added to the sample solution in the volume ratio of 1:5.

Apart from PVS, a polyglycol methyl ether and/or polyvinylpyrrolidone is preferably also added to the sample solution, the precipitation being especially well reproducible in the case of the use of this combination. The polyglycol methyl ether and/or the polyvinylpyrrolidone are preferably added to the sample solution in an amount of from 5 to 10% by volume.

In carrying out the process according to the present invention, it is important that divalent cations are not present in measurable amounts. However, in the case of amounts of divalent cations normally present in serum, which are usually only trace amounts, no disturbances occur so that this requirement can then be neglected. Hence, it is only necessary that the invention be performed in the substantial absence of divalent cations. Since, however, the appearance of abnormal samples with an unusually high content of divalent cations cannot be excluded, it is preferable to add not only the above-mentioned substances but also a complex former for polyvalent cations, polyaminoacetates, for example ethylenediamine-tetraacetic acid (EDTA), preferably being used for this purpose. Such a complex former is preferably added in an amount such that its concentration in the sample solution is 0.01 to 0.001 mole/liter.

The evaluation of the LDL fraction precipitated by the process according to the present invention is preferably carried out by using one of the methods known for the determination of lipoproteins. The cholesterol contained in the lipoprotein is preferably determined by means of processes known for that purpose, for example by oxidation with cholesterol oxidase and measurement of the hydrogen peroxide formed by the oxidation. This determination is preferably carried out either by determining the total content of cholesterol in the sample, as well as the cholesterol in the precipitation supernatant, the amount of LDL being deduced from the difference or by dissolving the LDL precipitate and determining the cholesterol in the solution thus obtained. The measured amount of cholesterol is analogous to the amount of lipoprotein since the amount of cholesterol in the lipoprotein fractions is constant.

The PVS is preferably used as the potassium salt but other monovalent cations, especially sodium, lithium and ammonium, can, however, be used in the same manner.

The present invention also provides a reagent for the determination of the $\beta$-lipoprotein fraction in body fluids, wherein it contains polyvinyl sulphate. It preferably also contains a polyvinyl methyl ether and/or polyvinylpyrrolidone. According to another preferred embodiment, the reagent also contains a complex former for polyvalent cations, a polyaminoacetate being especially preferred.

A typical reagent of the above-described preferred kind contains 0.1 to 0.01% by weight of polyvinyl sulphate, 5 to 10% by volume of polyglycol methyl ether and/or polyvinylpyrrolidone, as well as a complex former in a concentration of 0.01 to 0.001 mole, in each case referred to the volume of serum.

The process and reagent according to the present invention are especially simple and dependable. Comparison with the recognised but substantially more laborious methods of determination gave an excellent agreement of the results.

The following Example is given for the purpose of illustrating the present invention:

EXAMPLE (A) Preparation of the precipitation reagent

Solution I

PVS/polyethylene glycol methyl ether 34 ml. PVS solution (c=3 g./liter)
16 ml. polyethylene glycol methyl ether (M.W. 190–550)
50 ml. EDTA (0.01M)

Solution II

PVS/polyvinylpyrrolidone (Plasdone)
34 ml. PVS solution (c=3 g./liter)
16 ml. water
50 ml. EDTA (0.01M)
6.5 g. Plasdone, K 29-32

(B) Precipitation

Into a centrifuge glass pipette 200 μl. of sample and 100 μl. of precipitation reagent I or II, mix, leave to stand for 15 minutes at ambient temperature and centrifuge for 2 minutes at 10,000 g or for 15 minutes at 1500 g. After centrifuging, the supernatant, which has either a clear or turbid appearance, depending upon the VLDL and chylomicron content thereof, is separated off and used for the determination of the cholesterol by means of the CHOD-PAP method. The CHOD-PAP method depends upon the oxidation of cholesterol with cholesterol oxidase and photometric determination of the hydrogen peroxide thereby formed by the colour reaction with phenol and 4-aminoantipyrine.

(C) Cholesterol determination

| wavelength | Hg 546 nm (470-560 nm) |
| spectral photometer | 500 nm |
| cuvette | 1 cm layer thickness |
| incubation temperature | 20-25° C. or 37° C. | measurement against reagent blank (RB)

One reagent blank suffices for each series of measurements.

| into reagent glasses pipette | RB | sample |
|---|---|---|
| supernatant | — | 50 μl. |
| CHOD-PAP reagent | 2000 μl. | 2000 μl. | mix and incubate RB and sample for 20 minutes at 20° to 25° C. or for 12 minutes at 37° C. Within the course of 1 hour, measure the extinction of the sample against RB ($E_{sample}$).

It will be understood that the specification and examples are illustrative but not limitative of the present invention and that other embodiments within the spirit and scope of the invention will suggest themselves to those skilled in the art.

What is claimed is:

1. Method for the determination of the $\beta$-lipoprotein fraction (LDL) in body fluids which comprises selectively precipitating the LDL fraction from the body fluid sample by the addition of a polyvinyl sulfate with monovalent cations in the substantial absence of divalent cations, and then determining this LDL fraction.

2. Method as claimed in claim 1, wherein the body fluid is serum.

3. Method as claimed in claim 1, wherein the body fluid is plasma.

4. Method as claimed in claim 1, wherein a polyglycol methyl ether is additionally added to the sample.

5. Method as claimed in claim 1, wherein a polyvinylpyrrolidone is additionally added to the sample.

6. Method as claimed in claim 1, wherein said polyvinyl sulfate is a water-soluble polyvinyl sulfate at least 70% of the vinyl alcohol units of which carry a sulfate group.

7. Method as claimed in claim 1, wherein 0.1 to 0.01% wt./vol. of polyvinyl sulfate is added to said sample.

8. Method as claimed in claim 4, wherein said polyglycol methyl ether is added in an amount of 5 to 10% by volume of the sample.

9. Method as claimed in claim 5, wherein said polyvinylpyrrolidone is added in an amount of 5 to 10% by volume of the sample.

10. Method as claimed in claim 1, wherein said body fluid sample contains polyvalent cations, further comprising adding a complex former for polyvalent cations to reduce the divalent cation content.

11. Method as claimed in claim 10, wherein a polyaminoacetate is used as the complex former.

12. Method as claimed in claim 1, wherein the amount of LDL is determined by measuring the cholesterol content in either the precipitate or in the serum and supernatant.

* * * * *